United States Patent [19]

Lindemann et al.

[11] 4,231,903

[45] Nov. 4, 1980

[54] DETERGENT COMPOSITIONS

[75] Inventors: Martin K. O. Lindemann, Bridgewater; Robert J. Verdicchio, Succasunna, both of N.J.

[73] Assignee: Johnson & Johnson, New Brunswick, N.J.

[21] Appl. No.: 965,460

[22] Filed: Nov. 30, 1978

[51] Int. Cl.$^2$ .................... C11D 3/36; C11D 7/36
[52] U.S. Cl. ................... 252/545; 252/526; 252/546; 252/DIG. 7; 252/DIG. 13; 424/70; 260/924–925
[58] Field of Search ......... 252/545, 546, 526, DIG. 7, 252/DIG. 13; 424/70; 260/924–925

[56] References Cited

U.S. PATENT DOCUMENTS

| | | | |
|---|---|---|---|
| 2,999,069 | 9/1961 | Masci et al. | 252/548 |
| 3,058,836 | 9/1962 | Masci et al. | 252/545 |
| 3,928,251 | 12/1975 | Bolich, Jr. et al. | 252/545 |
| 3,950,417 | 4/1976 | Verdicchio et al. | 252/545 |

*Primary Examiner*—Mayer Weinblatt
*Attorney, Agent, or Firm*—Steven P. Berman

[57] ABSTRACT

An improved non-irritating or low irritating detergent composition exhibiting good foaming properties is disclosed. The composition is a synergistic mixture of an amphoteric surfactant and a phosphobetaine or phosphitaine surfactant.

10 Claims, No Drawings

DETERGENT COMPOSITIONS

BACKGROUND OF THE INVENTION

Detergent and cleansing compositions intended for use as personal cleansing products not only must exhibit cleansing action but they must also be non-irritating or have low irritation potential to the skin and the eyes. The major use for such compositions is in shampoos; but other uses include liquid skin cleansers, baby baths, bubble baths and the like. A suitable composition for use as a shampoo must remove the surface grease and leave the hair and scalp clean. In addition, it should leave the hair lustrous, soft and manageable; still further, it is desirable that it possess good lathering and foaming properties for consumer acceptability.

Synthetic detergents well known in the art include anionic, cationic, amphoteric and nonionic detergents or surfactants, as they are usually referred to. The surfactants generally exhibiting the most superior properties in terms of foaming, cleaning and end result attributes are the anionic detergents. Thus, most shampoo and cleansing formulations contain anionic surfactants as one of the active ingredients. These surfactants, however, have a tendency to be very irritating to the skin and the eyes in the levels normally utilized, i.e., above 10% by weight of the total composition. For this reason, anionic detergent compositions intended for personal use are modified by subsituting a significant amount of nonionic surfactants which are generally mild although of less effective cleansing ability. Certain amphoteric surfactants are reported to have a low eye irritation potential. In an article on "Baby Shampoos" by H. S. Mannheimer, American Perfumer, 76, 36-37 (1961), there is described surface active agents which are complexes of an anionic surface active agent and a particular amphoteric surface active agent which are argued to be non-irritating to the eyes. A number of similar compositions are available commercially and while they are milder than conventional shampoos, they are still found to be somewhat irritating or lacking in some other desired property. Thus, there is still a need for shampoo and other cleansing compositions in which irritancy can be substantially eliminated without sacrificing other desired properties such as cleansing and foaming attributes.

Several U.S. patents describe compositions in which both amphoteric and nonionic surfactants are incorporated in anionic surfactant compositions. Thus, in U.S. Pat. Nos. 2,999,069 and 3,055,836 there are described shampoo compositions comprising certain mixtures of ethoxylated anionic, amphoteric and polyethoxylated nonionic surfactants. Further, in U.S. Pat. No. 3,928,251 there are described shampoo compositions comprising certain mixtures of anionic, nonionic and zwitterionic surfactants. Similarly, in U.S. Pat. No. 3,950,417 shampoo compositions are described for which low ocular irritancy is claimed. In these compositions, nonionic and amphoteric surfactants have been added to modify anionic surfactants. All of these compositions include a nonionic surfactant as an essential component as well as an anionic surfactant and as mentioned above, these surfactants have various negatives.

SUMMARY OF THE INVENTION

It is an object of this invention to provide improved detergent and cleansing compositions.

It is a further object of this invention to provide improved detergent and cleansing compositions which exhibit low irritation potential to the eyes and skin.

It is a further object of this invention to provide improved detergent and cleansing compositions which exhibit good foaming properties including excellent foam stability.

Other objects of this invention will be set forth in or be apparent from the following detailed description of the invention.

The foregoing objects and other features and advantages of the present invention are achieved by detergent and cleansing compositions comprising a synergistic mixture of surfactants which exhibit low eye and skin irritancy and good foaming properties. More specifically, the present invention relates to detergent and cleansing compositions comprising a synergistic mixture of a specific amphoteric surfactant and a phosphobetaine or phosphitaine compound.

DETAILED DESCRIPTION OF THE INVENTION

In general, this invention comprises a synergistic mixture of a specific amphoteric surfactant and a specific phosphobetaine or phosphitaine surfactant in a ratio of from 1:4 to 4:1. The term "synergistic mixture" as used herein refers to a mixture of two discrete compounds which display a degree of foam stability which is greater than the sum of foam stability of the compounds taken individually.

The specific amphoteric compound which has been found useful in the present invention is of the formula

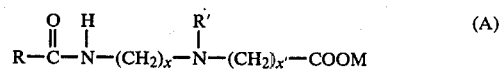

(A)

wherein R is an alkyl group containing from about 8 to 18 carbon atoms and mixtures thereof; R' is hydroxyalkyl containing from 2 to 4 carbon atoms or $CH_2-O-CH_2-COOM$; x and x' are integers from 1 to 5; and M is hydrogen or an alkali metal.

Particular preferred compounds would include those where R is lauric, a lauric-myristic blend or a so-called "stripped coconut" blend containing a mixture of from 10 to 18 carbon atoms; x is 2; x' is 1; R is hydroxyethyl and M is sodium. Amphoteric surfactants of this type are described in and can be prepared in accordance with the methods described in U.S. Pat. No. 2,970,160.

The amphoteric surfactants useful in the compositions of this invention are present in an amount of from about 1-20% by weight of the total composition, preferably from about 2-8%, provided, however, that the total amount of amphoteric surfactant and phosphobetaine or phosphitaine surfactant is not greater than about 35% by weight of the total composition, preferably from about 8-20%.

The phosphobetaine and phosphitaine surfactants which are useful in the present invention are novel compounds described and claimed in copending applications Ser. Nos. 965,461 and 965,462 filed Nov. 30, 1978 and Nov. 30, 1978, respectively, are are characterized as amphoteric and zwitterionic betaine compounds having at least one phosphorous-containing anion in the molecule.

The phosphobetaines are of the formula

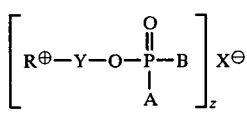

wherein

A is selected from $O^-$, OM and $-O-Y-R^{\oplus}$

B is selected from $O^-$ and $OM'$ $X^{\ominus}$ is an anion z is an integer from 0 to 2 with the proviso that only one of A and B can be $O^-$ and z is of a value necessary for charge balance (i.e., when A and B are $O^-$ and $OM'$, or OM and $O^-$, respectively, z is 0; when A and B are OM and $OM'$, or $-O-Y-R^{\oplus}$ and $O^-$, respectively, z is 1; when A is $-O-Y-R^{\oplus}$ and B is $OM'$, z is 2);

R is an amidoamine reactant moiety of the formula

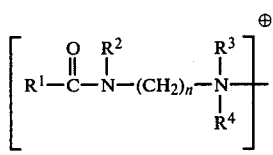

wherein $R^1$ is alkyl, alkenyl, alkoxy, or hydroxyalkyl of from 5 to 22 carbon atoms each, or aryl or alkaryl of up to 20 carbon atoms;

$R^2$ is hydrogen or alkyl, hydroxyalkyl or alkenyl of up to 6 carbon atoms each or cycloalkyl of up to 6 carbon atoms, preferably of from 2 to 5 carbon atoms, or polyoxyalkalene of up to 10 carbon atoms;

$R^3$ and $R^4$, which may be the same or different, are selected from alkyl, hydroxyalkyl, carboxyalkyl of up to 6 carbon atoms in each alkyl moiety, and polyoxyalkylene of up to 10 carbon atoms; in addition, $R^3$ and $R^4$ taken together with the nitrogen to which they are attached, may represent an N-heterocycle, e.g., a morpholino structure, in which the Y radical is bonded to a ring atom of said N-heterocycle other than the nitrogen of the R moiety;

n is an integer from 2 to 12;

The term "polyoxyalkalene radical" as used above in the definition of $R^2$, $R^3$ and $R^4$ may be of the formula $(R^5-O-R^{5'})_m$, wherein $R^5$ and $R^{5'}$ are alkyl of from 1 to 4 carbon atoms and m is an integer from about 2 to 10.

In addition to the foregoing definitions wherein R is amidoamine, R may be an N-heterocyclic radical which may contain one additional hetero atom (e.g., oxygen sulfur or another nitrogen) and contains 5 to 6 total ring carbon atoms; optionally said heterocyclic radical may be substituted with alkyl and/or hydroxyalkyl of up to 20 carbon atoms each. Typical of such N-heterocyclic radicals are imidazolyl, N-alkylmorpholino, alkylpyrimidino, alkyloxazolinyl, and the like. Such compounds may be represented by the formula

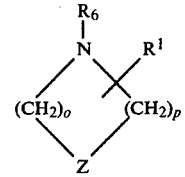

wherein

Z is N, S or O;

o is an integer from 0 to 3;

p is an integer from 1 to 3;

provided that the sum of o+p is from 3 to 4;

$R^1$ is defined as before and is linked to a ring carbon atom; and $R_6$ is alkyl of from 2 to 6 carbon atoms which may be substituted with a hydroxyl group at the terminal or a non-terminal carbon atom;

Y may be alkylene, optionally interrupted by up to 3 oxygen atoms, of up to 12 carbon atoms, which alkylene chain may optionally be substituted with lower-alkyl, alkoxy, hydroxy or hydroxyalkyl, e.g., of not more than 10 carbon atoms each.

M and $M'$, which may be the same or different, are (a) hydrogen, (b) an organic radical selected from alkyl or hydroxyalkyl of up to 6 carbon atoms, polyhydroxyalkyl of up to 10 carbon atoms, glyceryl, cycloalkyl of up to 6 carbon atoms, aryl or arylalkyl of up to 10 carbon atoms, or (c) a salt radical selected from alkali metals (e.g., sodium or potassium), alkaline earth metals (e.g., magnesium or calcium), and mono-, di-, or triethanolamine. With reference to formula (I) above, wherein both M and $M'$ are contained, there is the proviso that when either M or $M'$ is an organic radical (b), the other of M and $M'$ must be hydrogen or a salt radical (c).

The phosphitaines are of the formula

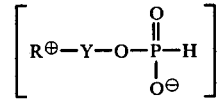

wherein R and Y are as defined above.

The phosphobetaine compounds and phosphitaine compounds described above can be prepared in accordance with the processes described in copending applications Ser. Nos. 965,461 and 965,462, filed Nov. 30, 1978 and Nov. 30, 1978, respectively, the teachings of which are incorporated herein by reference.

Representative phosphobetaine and phosphitaine compounds useful in the present invention include compounds having the following structures:

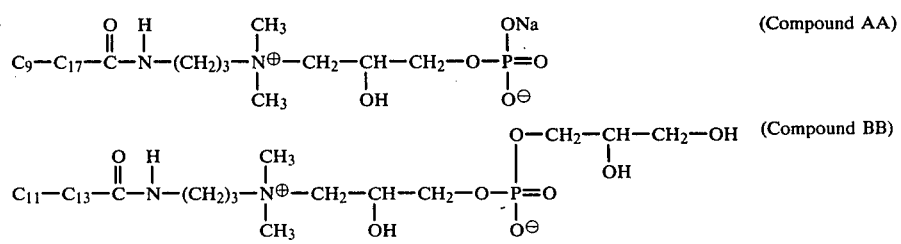

-continued

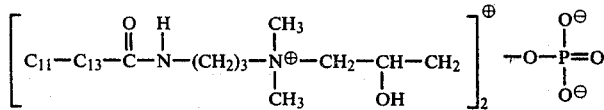  (Compound CC)

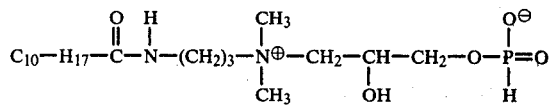  (Compound DD)

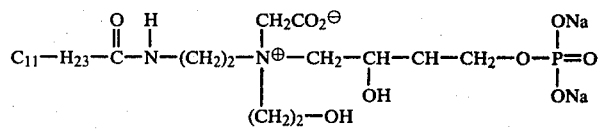  (Compound EE)

The phosphobetaine and phosphitaine surfactants useful in the compositions of this invention are present in an amount of from about 1–20% by weight of the total composition, preferably about 2–8%, provided, however that the total amount of amphoteric surfactant and phosphobetaine and/or phosphitaine surfactant is not greater than about 35% by weight of the total composition, preferably from about 8–20%.

Further, to achieve the desired results of the present invention, the amphoteric surfactant should be in a weight ratio of from about 4:1 to 1:4 to the phosphobetaine and/or phosphitaine surfactant, preferably about 2:1 to 1:2.

If desired, from about 1–4% by weight of the total composition of an anionic surfactant can be added without adversely affecting the low ocular irritation potential of the compositions.

It is envisioned that any anionic surfactant may be used in the above-specified limited amounts in compositions of the invention such as, for example, an alkyl sulfate of the formula R—CH$_2$—OSO$_3$X, an alkylether sulfate of the formula R(OCH$_2$CH$_2$)$_p$—OSO$_3$X, an alkylmonoglyceryl ether sulfonate of the formula

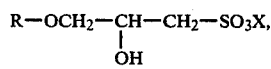

an alkylmonoglyceride sulfate of the formula

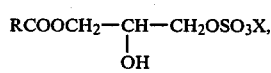

an alkylmonoglyceride sulfonate of the formula

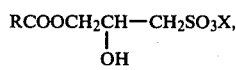

an alkyl sulfonate of the formula RSO$_3$X, an alkylaryl sulfonate of the formula

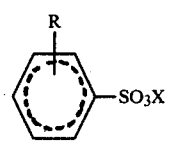

an alkyl sulfosuccinate of the formula

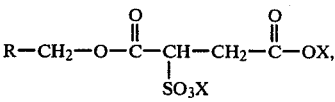

an alkyl sarcosinate of the formula

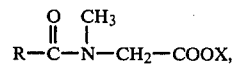

an acyl isothionate of the formula

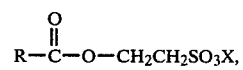

an alkyl methyl tauride of the formula

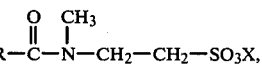

a fatty acid protein condensate of the formula

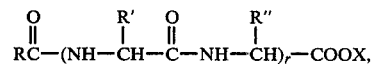

an alcohol ether carboxylate of the formula RO(CH$_2$CH$_2$O)$_q$—CH$_2$CO$_2$X and the like; wherein R is higheralkyl having from 7 to 17 carbon atoms; R' and R" are members each selected from the group consisting of hydrogen, loweralkyl, hydroxyloweralkyl, thioloweralkyl, carboxyloweralkyl, aminoloweralkyl, benzyl, and p-hydroxybenzyl; X is a member selected from the group consisting of alkali metal ions, alkaline earth metal ions, ammonium ions, and ammonium ions substituted with from 1 to 3 loweralkyls; p is an integer from about 3 to about 6; q is an integer from 2 to about 6 and r is an integer from 2 to 10.

The preferred type of anionic surfactant is an alkyl ether sulfate, more preferably sodium tridecylalcohol ether sulfate in which p is 1 to 5.

In addition to the surfactants, other ingredients conventionally added to detergent and cleansing compositions for personal use, such as dyes, preservatives, perfumes, thickeners, opacifiers, conditioners, emollients, buffering agents and the like, may be added in minor amounts. Ingredients such as dyes, preservatives and perfumes together usually constitute less than 2% by weight of the total composition in an amount of from about 1 to about 3% by weight of the total composition.

The detergent and cleansing compositions of the present invention may be concentrate compositions which are subsequently modified by dilution with water or other diluents to provide the ultimate compositions for use or they may be the ultimate cleansing compositions to be employed without modification. The compositions of the present invention are primarily useful in shampoo formulations where high foaming characteristics as well as low ocular and skin irritation potential are desired. They may also be used as liquid soaps and cleansers such as baby bath compositions, in bubble bath compositions, as well as in compositions suitable for cleansing animals and inanimate objects.

The aforementioned detergent and cleansing compositions are prepared by admixing the phosphobetaine and/or phosphitaine with the amphoteric surfactant at room temperature or slightly elevated temperatures (about 50° C.) and then sufficient deionized water is added to bring the composition to about three-quarters of its intended weight. The pH is adjusted to within the range of 5 to 8, preferably 6 to 8, by adding strong acid, e.g., HCL, or strong base, e.g., NaOH, as needed. Other ingredients such as viscosity builders, preservatives, dyes, perfumes and the like are incorporated prior to adjusting the pH and adding the remainder of the water.

The detergent and cleansing composition of the present invention can be tested for ocular irritation by the following modified Draize Test (J. H. Draize et al., Toilet Goods Assn. No. 17, May 1952, No. 1 Proc. Sci. Sect.).

An 0.1 ml sample of a neutral composition under test is dropped into one eye of an albino rabbit, the other eye serving as a control. Six rabbits are employed for each composition. Observations are made after 1, 24, 48, 72 and 96 hours and 7 days after initial instillation; second and third instillations are made after the 24 and 48 hour readings. Results may vary from substantially no change or only a slight irritation in the appearance of the rabbit's eye after 7 days to severe irritation and/or complete corneal opacity. Ocular lesions are scored for the cornea, iris and conjunctiva with a higher number indicating greater ocular irritation and the scores are added to give a total numerical value for each reading for 6 rabbits and averaged. The averaged score is an indication of the irritation potential of the composition under test. Based on the averaged score, descriptive irritation evaluation may be given, e.g., none, slight, moderate, severe, as the case may be.

The detergent and cleansing compositions of the invention provide high foam volume and moreover outstanding foam stability as measured by an adaption of the well-known Ross-Miles foam test principle ["Oil and Soap" 18.99–102 (1942)]:

Lanolin, anhydrous, cosmetic grade is mixed with dioxane (technical grade) in the proportion of 2.5 grams lanolin and 100 grams of dioxane. The lanolin is first mixed with 25 cc. of dioxane. This mixture is heated over a steam bath to 45° C. in order to dissolve the lanolin in the dioxane. The remainder of the dioxane is then added and mixed. This lanolin-dioxane solution, which is stored in an amber bottle, should be prepared fresh on the day that the tests are run.

The composition to be tested is diluted by adding 376 cc. of distilled water to 4 grams of the composition, and then by adding 20 cc. of the lanolin-dioxane solution described above while mixing. Heat is produced when the lanolin-dioxane solution is added to the solution of the composition in water and care must be taken in adjusting the temperature of this solution to 24°–25° C. Both of these intermediate solutions should therefore be adjusted to 23° C. before mixing. The cooling of the lanolin-dioxane solution should be gradual in order to avoid precipitation of the lanolin. This will produce a final solution with a temperature of 24°–25° C.

The final solution of the composition to be tested, water, dioxane and lanolin described above, is then run in a modified Ross-Miles foam column in the usual way. All tests are conducted in duplicate, and the average of the two results is taken. Foam stability is determined by measuring the decay in foam height after two minutes, expressed as a percentage of the original height.

Specific embodiments of the detergent and cleansing compositions prepared in accordance with the present invention are illustrated by the following representative examples. It will be understood, however, that the invention is not confined to the specific limitations set forth in the individual examples, but rather to the scope of the appended claims.

EXAMPLE I

A shampoo composition is prepared by charging 400 grams of deionized water, 150 grams of a 30% active solution of Compound EE and 150 grams of a 30% active solution of an amphoteric surfactant of the formula

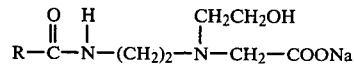

(wherein R is a 70-30 mixture lauric myristic) with agitation in a suitable vessel. 30 grams of glycerine and 10 grams of polyethylene glycol 6000 distearate are then added and the mixture is heated to 60° C. for a period of twenty minutes and then cooled to 40°–50° C. and the pH adjusted to 7.0–7.2 with 20 grams of 15% HCL. The resulting solution is allowed to cool to 35° C. and then the dyes, preservatives and fragrance are added and a sufficient quantity of deionized water to yield a total solution of 1000 grams of the desired composition consisting of the following ingredients:

|  | wt./wt. % |
| --- | --- |
| Compound EE | 4.500 |
| amphoteric | 4.500 |
| glycerine | 3.000 |
| polyethylene glycol 6000 distearate | 1.000 |
| dye | 0.002 |
| preservative | 0.200 |
| fragrance | 0.200 |
| 15% HCL | 2.000 |
| deionized water | q.s. to 100% |

The above composition is tested for ocular irritation in accordance with the above-described modified Draize test and found to be a slight irritant. Still further, when the above shampoo composition is tested according to the above-described modified Ross-Miles test, it exhibits good foam volume and a percent foam decay of less than 15%.

EXAMPLE II

A baby bath composition is prepared by charging 200 grams of deionized water, 71 grams of a 35% active solution of Compound AA and 83 grams of a 30% active solution of a "stripped coco" amphoteric of the formula

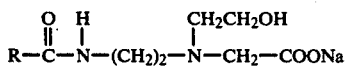

(wherein R is a mixture of chain lengths of from 10–18 carbon atoms) in a suitable vessel with agitation. To this mixture is added 10 grams of polyethylene glycol 6000 distearate, 0.5 grams of Versene 100, 20 grams of propylene glycol and 20 grams of polyvinyl pyrrolidine and the mixture heated to 60° C. for 30 minutes. The solution is then cooled to 35° C. and the pH adjusted to 6.5 with 10 grams of 15% HCL. Fragrance, preservatives and dyes are added and sufficient deionized water to yield a total solution of 1000 grams of the desired composition consisting of the following ingredients:

|  | wt./wt. % |
| --- | --- |
| Compound AA | 2.500 |
| "stripped coco" amphoteric | 2.500 |
| propylene glycol | 2.000 |
| Versene 100 | 0.500 |
| polyvinyl pyrrolidine | 2.000 |
| polyethylene glycol 6000 distearate | 1.000 |
| dye | 0.001 |
| preservative | 0.200 |
| fragrance | 0.200 |
| 15% HCL | 2.500 |
| deionized water | q.s. to 100% |

The above composition is tested for ocular irritation in accordance with the above-described modified Draize test and found to be a slight irritant. Still further, when the above baby bath composition is tested according to the above-described modified Ross-Miles test, it exhibits good foam volume and a percent foam decay of less than 10%.

Liquid detergent cleansing compositions consisting of the following ingredients are prepared in accordance with the general procedure of EXAMPLE I:

|  | % w/w | | | | | | | |
| --- | --- | --- | --- | --- | --- | --- | --- | --- |
|  | III | IV | V | VI | VII | VIII | IX | X |
| Compound EE | 10 | — | — | 5 | — | 6 | — | 3 |
| Compound AA | — | 10 | — | — | 5 | — | — | — |
| amphoteric of EXAMPLE I | — | — | 10 | 5 | 5 | — | 6 | 3 |
| deionized water | q.s. to 100 | q.s. to 100 | q.s. to 100 | q.s. to 100 | q.s. to 100 | q.s. to 100 | q.s. to 100 | q.s. to 100 |

These compositions all exhibit low ocular and skin irritation and excellent foam volume. These compositions are tested for foam stability by means of the modified Ross-Miles foam test as described hereinbefore and the results are reported below in Table I:

TABLE I

| Composition | % Foam Decay |
| --- | --- |
| EXAMPLE III | 17 |
| EXAMPLE IV | 60 |
| EXAMPLE V | 20 |
| EXAMPLE VI | 14 |
| EXAMPLE VII | 11 |
| EXAMPLE VIII | 40 |

TABLE I-continued

| Composition | % Foam Decay |
| --- | --- |
| EXAMPLE IX | 40 |
| EXAMPLE X | 12 |

As can be readily seen from the results in Table I, the compositions containing a mixture of amphoteric surfactant and phosphobetaine surfactant (EXAMPLES VI, VII and X) exhibit a synergistic decrease in % Foam Decay indicating excellent foam stability.

In addition to the preferred embodiments described herein, other embodiments, arrangements and variations within the spirit of the invention and the scope of the appended claims will occur to those skilled in the art.

What is claimed is:

1. A low irritating detergent and cleansing composition wherein the active ingredients consist essentially of
   (a) from about 1 to 20% by weight of the total composition of an amphoteric surfactant of the formula

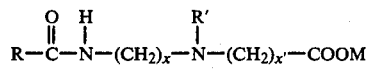

wherein R is an alkyl group containing from about 8 to 18 carbon atoms and mixtures thereof; R' is hydroxy alkyl containing from 2 to 4 carbon atoms or $CH_2-O-CH_2-COOM$; x and x' are integers from 1 to 5; and M is hydrogen or an alkali metal; and
   (b) from about 1 to 20% by weight of the total composition of a compound selected from the group consisting of a phosphobetaine of the formula

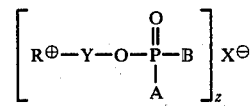

wherein
A is selected from $O^-$, OM and $-O-Y-R^{\oplus}$
B is selected from $O^-$ and OM'
$X^{\ominus}$ is an anion
z is an integer from 0 to 2
with the proviso that only one of A and B can be $O^-$ and z is of a value necessary for charge balance;
R is an amidoamine reactant moiety of the formula

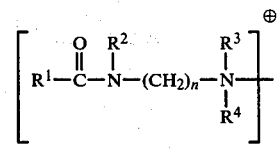

wherein
$R^1$ is alkyl, alkenyl, alkoxy, or hydroxyalkyl of from 5 to 22 carbon atoms each, or aryl or alkaryl of up to 20 carbon atoms;
$R^2$ is hydrogen or alkyl, hydroxyalkyl or alkenyl of up to 6 carbon atoms each or cycloalkyl of up to 6 carbon atoms, or polyoxyalkalene of up to 10 carbon atoms;

R³ and R⁴, are the same or different and are selected from alkyl, hydroxyalkyl, carboxyalkyl of up to 6 carbon atoms in each alkyl moiety, and polyoxyalkylene of up to 10 carbon atoms; in addition, R³ and R⁴ taken together with the nitrogen to which they are attached, may represent an N-heterocycle, structure in which the Y radical is bonded to a ring atom of said N-heterocycle other than the nitrogen of the R moiety;
n is an integer from 2 to 12; or
R is an N-heterocyclic radical of the formula

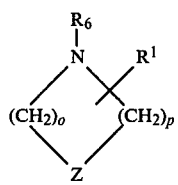

wherein
Z is N, S or O;
o is an integer from 0 to 3;
p is an integer from 1 to 3;
provided that the sum of o+p is from 3 to 4;
R¹ is defined as before and is linked to a ring carbon atom; and
R₆ is alkyl of from 2 to 6 carbon atoms
Y is alkylene, of up to 12 carbon atoms
M and M', which may be the same or different, are (a) hydrogen, (b) an organic radical selected from alkyl or hydroxyalkyl of up to 6 carbon atoms, polyhydroxyalkyl of up to 10 carbon atoms, glyceryl, cycloalkyl of up to 6 carbon atoms, aryl or arylalkyl of up to 10 carbon atoms, or (c) a salt radical selected from alkali metals, alkaline earth metals, and mono-, di-, or tri-ethanolamine, provided that when either M or M' is an organic radical (b), the other M and M' must be hydrogen or a salt radical (c);
or a phosphitaine of the formula:

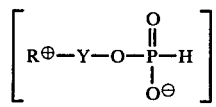

R and Y are as defined above;
wherein the total of (a) and (b) does not exceed about 35% by weight of the total composition.

2. The composition of claim 1 wherein the phosphobetaine compound is of the formula

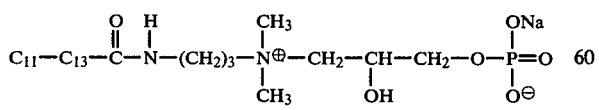

3. The composition of claim 1 wherein the phosphobetaine compound is of the formula

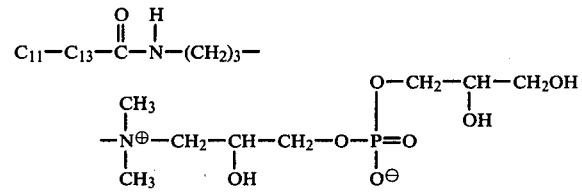

4. The composition of claim 1 wherein the phosphobetaine compound is of the formula

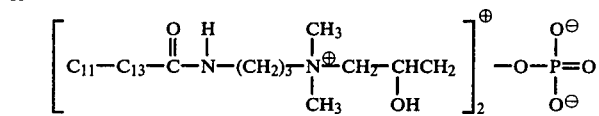

5. The composition of claim 1 wherein the phosphitaine compound is of the formula

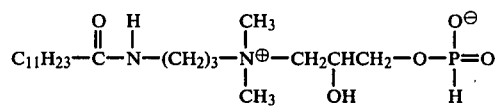

6. The composition of claim 1 wherein the phosphobetaine compound is of the formula

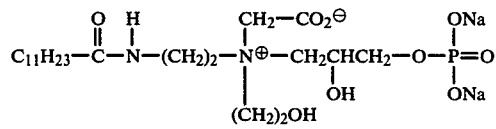

7. The composition of claim 1 wherein the amphoteric and phosphobetaine or phosphitaine are in a weight ratio of from about 1:4 to 4:1.

8. The composition of claim 1 wherein the total weight of the amphoteric and phosphobetaine or phosphitaine is from about 8 to 20% by weight of the total composition.

9. The composition of claim 1 wherein the amphoteric is of the formula

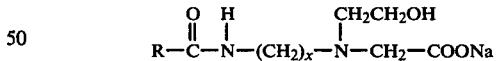

wherein R is a mixture of from 10 to 18 carbon atoms.

10. The composition of claim 9 containing from about 1 to 4% by weight of the total composition of an anionic surfactant selected from the group consisting of alkyl sulfate, alkylether sulfate, alkylmonoglyceryl ether sulfonate, alkylmonoglyceride sulfate, alkylmonoglyceride sulfonate, alkyl sulfonate, alkylaryl sulfonate, alkyl sulfosuccinate, alkyl sarcosinate, acyl isothionate, alkyl methyl tauride, fatty acid protein condensate and an alcohol ether carboxylate.

* * * * *